United States Patent
Kim et al.

(10) Patent No.: US 12,052,956 B2
(45) Date of Patent: Aug. 6, 2024

(54) PLANT REGENERATION MEDIUM COMPOSITION AND PLANT REGENERATION METHOD USING THE SAME

(71) Applicant: WELLSPRING CORPORATION, Seoul (KR)

(72) Inventors: Tae Yoon Kim, Seongnam-si (KR); Seung Yop Lee, Seoul (KR); Han Bok Seo, Seoul (KR); Sang Hyo Lee, Seongnam-si (KR)

(73) Assignee: WELLSPRING CORPORATION, Seoul (KR)

( * ) Notice: Subject to any disclaimer, the term of this patent is extended or adjusted under 35 U.S.C. 154(b) by 0 days.

(21) Appl. No.: 17/433,645

(22) PCT Filed: Feb. 27, 2020

(86) PCT No.: PCT/KR2020/002818
§ 371 (c)(1),
(2) Date: Aug. 25, 2021

(87) PCT Pub. No.: WO2020/180053
PCT Pub. Date: Sep. 10, 2020

(65) Prior Publication Data
US 2022/0142056 A1 May 12, 2022

(30) Foreign Application Priority Data
Mar. 5, 2019 (KR) .................. 10-2019-0025300

(51) Int. Cl.
*A01G 7/06* (2006.01)

(52) U.S. Cl.
CPC ..................... *A01G 7/06* (2013.01)

(58) Field of Classification Search
CPC .................. A01H 4/002; A01G 7/06
See application file for complete search history.

(56) References Cited

FOREIGN PATENT DOCUMENTS

| JP | H03-139224 A | 6/1991 |
|----|--------------|--------|
| KR | 10-2011-0118191 A | 10/2011 |

OTHER PUBLICATIONS

Dallakyan et al. Moscow University Biological Sciences Bulletin, vol. 72, No. 3, pp. 115-120 (Year: 2017).*
Sajo et al. Oxidative Medicine and Cellular Longevity, Article ID 7340143, 11 pages (Year: 2017).*
Selvaraj et al. Scientia Horticulturae 112: 2-8 (Year: 2007).*
Dallakyan et al. Inland Water Biology, vol. 11, No. 1, pp. 103-107 (Year: 2018).*
G. A. Dallakyan et al., The Combined Effect of Shungite and Heavy Metals on the Growth of Microalgae Population, Inland Water Biology, 2018, pp. 103-107, vol. 11, No. 1.

* cited by examiner

*Primary Examiner* — Keith O. Robinson
(74) *Attorney, Agent, or Firm* — Goldilocks Zone IP Law

(57) ABSTRACT

The present invention relates to a plant regeneration medium composition and a plant regeneration method using same. More specifically, the present invention relates to a plant regeneration medium composition using a medium composition containing Shungite as an active ingredient to increase the rates of shoot organogenesis and root organogenesis, thereby shortening the time required for organogenesis using a plant explant and improving the efficiency of ontogeny, and to a plant regeneration method using same.

2 Claims, No Drawings

PLANT REGENERATION MEDIUM COMPOSITION AND PLANT REGENERATION METHOD USING THE SAME

CROSS-REFERENCE TO RELATED APPLICATIONS

This application claims the benefit under 35 U.S.C. section 371, of PCT International Application No.: PCT/KR2020/002818, filed on Feb. 27, 2020, which claims foreign priority to Korean Patent Application No.: KR10-2019-0025300, filed on Mar. 5, 2019, in the Korean Intellectual Property Office, both of which are hereby incorporated by reference in their entireties.

TECHNICAL FIELD

The present invention relates to a plant regeneration medium composition and a plant regeneration method using same. More specifically, the present invention relates to a plant regeneration medium composition using a medium composition containing Shungite as an active ingredient to increase the rates of shoot organogenesis and root organogenesis, thereby shortening the time required for organogenesis using a plant explant and improving the efficiency of ontogeny, and to a plant regeneration method using same.

BACKGROUND ART

Genetically Modified Organism (GMO) refers to agricultural products that are manipulated through genetic engineering to have traits or genes that cannot be expressed by conventional breeding methods. The cultivation area and crop diversity of GMOs are rapidly increasing due to increased yield and ease of distribution and processing of GMOs. GMOs are produced through various methods. For example, agrobacterium, a gene gun, inorganic mediators, floral dipping, etc. are used. In most of the cases, after induction of a callus from an explant of a plant, a plant regeneration process that induces shoot organogenesis and root organogenesis is required. For the plant regeneration, a medium containing specific hormones, carbon sources, and the like is used as disclosed in patent documents described below.

PATENT DOCUMENT

Korean Patent Application Publication No. 10-2011-0118191 (published on Oct. 31, 2011), titled "Direct High-frequency Regeneration Method of Shoots from Dry Maria Codata Leaves, and Plants Obtained Thereby"

However, conventional plant regeneration methods have problems in that the efficiency of ontogeny is low and the execution time (for example, 15 to 20 weeks for herbaceous crops) is long. Accordingly, there is an increasing need for a technology capable of reducing the time required for plant regeneration and of improving the efficiency of ontogeny.

DISCLOSURE

Technical Problem

The present invention has been devised to solve the aforementioned problems.

The objective of the present invention is to provide a plant regeneration medium composition and a plant regeneration method using same, the plant regeneration medium composition uses a medium composition containing Shungite as an active ingredient to increase the rates of shoot organogenesis and root organogenesis, thereby shortening the time required for organogenesis using a plant explant and improving the efficiency of ontogeny.

Technical Solution

The aforementioned objective of the present invention is achieved by embodiments described below.

According to one embodiment of the present invention, a medium composition for plant regeneration contains Shungite as an active ingredient.

According to another embodiment of the present invention, a medium composition for plant regeneration contains Shungite as an active ingredient, thereby promoting induction of shoot organogenesis of a plant.

According to a further embodiment of the present invention, a medium composition for plant regeneration contains Shungite as an active ingredient, thereby promoting induction of root organogenesis of a plant.

According to a yet further embodiment of the present invention, in the medium composition for plant regeneration, the Shungite may be contained in a concentration of 0.032 to 5 g/L.

According to a yet further embodiment of the present invention, in the medium composition for plant regeneration, the plant may be any one selected from the group consisting of cucumbers, chrysanthemums, and tomatoes.

According to a yet further embodiment of the present invention, in the medium composition for plant regeneration, the Shungite is pulverized to be used in a powder form.

According to a yet further embodiment of the present invention, a plant regeneration method includes an explant preparation step of obtaining explants from a plant, and an organogenesis step of culturing the explants in a medium containing Shungite as an active ingredient.

Advantageous Effects

The aforementioned embodiments of the present invention provide the advantages described below.

The present invention uses a medium composition containing Shungite as an active ingredient to increase the rates of shoot organogenesis and root organogenesis, thereby shortening the time required for organogenesis from a plant explant and improving the efficiency of ontogeny.

BEST MODE

Hereinafter, a plant regeneration medium composition according to the present invention and a plant regeneration method using the same according to the present invention will be described with reference to the accompanying drawings. Unless otherwise specified, all terms used in the present specification have the same meaning as the general meaning of the terms understood by a person with ordinary skill in the art to which the present invention belongs, and if the general meaning conflicts with the meaning of a term used in the present specification, the definition used in the present specification is applied. Moreover, detailed descriptions of well-known functions and configurations, which may unnecessarily obscure the gist of the present invention, will be omitted. In the entire specification, when it is described that one part "includes" some components, it does not mean that other components are excluded but means that other elements may be further included if there is no specific contrary description.

According to one embodiment of the present invention, a plant regeneration medium composition contains Shungite as an active ingredient. As described above, when a plant regeneration process involving a primary step of inducing a callus from an explant of a plant and a secondary step of inducing shoot organogenesis and root organogenesis is performed in a conventional manner of using an existing medium composition, the efficiency of organogenesis is low, and it takes a long time to perform the plant regeneration process. However, since the present invention uses a medium composition containing Shungite as an active ingredient to dramatically increase the rates of shoot organogenesis and root organogenesis, it is possible to shorten the time required for plant regeneration and increase the efficiency of ontogeny.

Shungite is a non-toxic natural mineraloid. In the present invention, the Shungite is used in a powder form composed of particles having sizes equal to or smaller than 3 mm. The content of the Shungite in the composition is preferably in a range of 0.032 to 5 g/L and more preferably in a range of 0.25 to 2 g/L.

The medium composition contains fundamental nutrients for plant growth (for example, MS salt, etc.), a carbon source (for example, Sucrose, etc.), a cytokinin-based hormone (for example, BA, BAP, Zeatin, etc.), an auxin-based hormones (for example, IBA, IAA, NAA, etc.), and distilled water. That is, the plant regeneration medium composition of the present invention is prepared by adding 0.032 to 5 g of Shungite per 1 L of distilled water to a medium composition comprising plant growth fundamental nutrients, a carbon source, a cytokinin-based hormone, an auxin-based hormone, distilled water, and the like. The plant regeneration medium composition of the present invention dramatically increases the rates of shoot organogenesis and root organogenesis due to the presence of the Shungite, thereby reducing the time required for plant regeneration and improving the efficiency of ontogeny.

It is possible to regenerate a variety of known plants including cucumbers, chrysanthemums and tomatoes, using the medium composition. The Cucurbitaceae family including watermelon, melon, pumpkin, and cucumber are known to have low regeneration efficiency. Specifically, cucumber regeneration is known to be the most difficult. An experiment described below shows that cucumbers were successfully regenerated using the medium composition of the present invention. Therefore, it is expected that the medium composition of the present invention can be successfully used for the regeneration of various plants.

A plant regeneration method according to another embodiment of the present invention includes an explant preparation step of obtaining explants from a plant and an organogenesis step of culturing the explants in a medium using a medium composition to differentiate them into organs.

The explant preparation step is a step of obtaining explants from a plant. For example, the explants may be obtained by culturing sterilized seeds in a germination medium or by sterilizing leaves of plants.

The organogenesis step is a step of culturing the explant obtained in the explant preparation step in a medium including a medium composition so that organs can be formed. The organogenesis step includes a shoot organogenesis step and a root organogenesis step. As the medium composition, the medium composition described above may be used.

The shoot organogenesis step is a step of inducing shoots by culturing the explants obtained in the explant preparation step in a shoot organogenesis induction medium. A composition used as the shoot organogenesis induction medium includes distilled water, fundamental nutrients for plant growth, carbon sources, plant growth hormones, Shungite, and the like. The Shungite is used in the form of powder. The particles in the powder have sizes equal to or smaller than 3 mm. The content of the Shungite in the composition is preferably in a range of 0.032 to 5 g/L and more preferably in a range of 0.25 to 2 g/L.

The root organogenesis step is a step of inducing formation of roots by culturing the explants transferred from the shoot organogenesis induction medium in a root organogenesis induction medium after the root organogenesis step is performed. A composition used as the root organogenesis induction medium includes distilled water, fundamental nutrients for plant growth, carbon sources, plant growth hormones, Shungite, and the like. The Shungite is used in the form of powder. The particles in the powder have sizes equal to or smaller than 3 mm. The content of the Shungite in the composition is preferably in a range of 0.032 to 5 g/L and more preferably in a range of 0.25 to 2 g/L. In the shoot organogenesis step, only the shoots are formed. However, in the root organogenesis step, the roots are formed as well as the shoots are continuously formed. In the present invention, a specific concentration of Shungite is contained in each of the shoot organogenesis induction medium and the root organogenesis induction medium so that the rates of the shoot organogenesis and the root organogenesis can be increased. This results in a reduction in plant regeneration time and improvement in ontogeny efficiency.

Hereinafter, the present invention will be described in more detail with reference to examples. However, these examples are presented merely for describing the present invention in more detail, and the scope of the present invention is not limited to these examples.

<Example 1> Regeneration of Cucumber

1. Preparation of Explant (1) Cucumber seeds (available from Hungnong Seeds Co.) from which the seed coat was removed were treated in 70% ethanol for 1 minute, washed with distilled water, treated with 1% sodium hypochloride for 15 minutes, and washed with distilled water to prepare sterilized seeds.

(2) The sterilized cucumber seeds were sown into a germination medium adjusted to pH 5.6 and incubated for 5 days in a growth chamber under conditions of a temperature of 25° C., a humidity of 50%, and a photoperiodic cycle of 16-hours light treatment and 8-hours dark treatment. The germination medium was prepared by mixing 4405.18 mg of MS salt (manufactured by Duchefa), 30 g of sucrose (manufactured by Duchefa), 500 mg of MES (manufactured by Duchefa), and 8 g of phyto agar (manufactured by Duchefa), per 1 L of distilled water.

(3) Cotyledons obtained through the incubation were cut into pieces having a size of 0.5 $cm^2$ to prepare explants.

2. Regeneration of Explant (Shoot Induction and Root Induction)

(1) For shoot induction, the explants were transferred to the shoot induction medium and then cultured for 4 weeks in a growth chamber under conditions of a temperature of 25° C., a humidity of 50%, and a photoperiodic cycle of 16-hours light treatment and 8-hours dark treatment. The shoot induction medium (pH 5.7) was prepared by mixing 4405.18 mg of MS salt (manufactured by Duchefa), 30 g of sucrose (manufactured by Duchefa), 3.2 mg of BAP (manufactured by Sigma), 0.5 mg of IBA (manufactured by Sigma), 500 mg of MES (manufactured by Duchefa), 8 g of phyto agar (manufactured by Duchefa), and Shungite, per 1 L of distilled water. The Shungite was produced near Lake Onega and purchased from the Karelian Shungite Factory in Russia. The Shungite was pulverized and screened through a screen with a mesh size of 1 to 3 mm to obtain a Shungite powder. The Shungite powder added to each medium composition was varied. The amounts of 0 g, 0.032 g, 0.25 g, 2 g, and 15 g of the Shungite powder were added to the respective medium compositions, per 1 L of distilled water.

(2) For root induction, the explants were transferred to the root induction medium from the shoot induction medium and then cultured for 4 weeks in a growth chamber under conditions of a temperature of 25° C., a humidity of 50%, and a photoperiodic cycle of 16-hours light treatment and 8-hours dark treatment. The root induction medium (pH 5.7) was prepared by mixing 4405.18 mg of MS salt (manufactured by Duchefa), 30 g of sucrose (manufactured by Duchefa), 500 mg of MES (manufactured by Duchefa), 8 g of phyto agar (manufactured by Duchefa), and Shungite, per 1 L of distilled water. The Shungite was produced near Lake Onega and purchased from the Karelian Shungite Factory in Russia. The Shungite was pulverized and screened through a screen with a mesh size of 1 to 3 mm to obtain a Shungite powder. The Shungite powder added to each medium composition was varied. The amounts of 0 g, 0.032 g, 0.25 g, 2 g, and 15 g of the Shungite powder were added to the respective medium compositions, per 1 L of distilled water. In each of the shoot induction medium and the root induction medium, the same amount of Shungite was used. For example, when 0.032 g/L of Shungite was used for the shoot induction medium, 0.032 g/L of Shungite was also used for the root induction medium.

3. Evaluation of Cucumber Regeneration Efficiency (1) After the shoot induction from the explants (4 weeks after the beginning of explant regeneration), the number of explants with callus and the number of explants with shoots were counted. In addition, after the root induction from the explants (8 weeks after from the beginning of explant regeneration), the number of explants with shoots and the number of explants with roots were counted. The counted numbers were compared with the number of explants used for plant regeneration and are shown in Table 1.

(2) Referring to Table 1, when 0.25 to 2 g/L of Shungite is additionally included in the shoot induction medium and the root induction medium used in the process of regeneration of cucumber explants, the shoot formation rate and the root formation rate were remarkably increased within an earlier period (i.e., 8 weeks) which is shorter than a typical cucumber regeneration period (i.e., 14 to 16 weeks). The Cucurbitaceae family including watermelon, melon, pumpkin, and cucumber are known to have low regeneration efficiency. Specifically, cucumber regeneration is known to be the most difficult. However, cucumbers were successfully regenerated in a shorter period when the medium composition of the present invention was used. Therefore, it is expected that the medium composition of the present invention can be successfully used for fast regeneration of various plants.

TABLE 1

| Shungite (g/L) | Proportion (%) of explants with callus after 4 weeks | Proportion (%) of explants with shoots after 4 weeks | Proportion (%) of explants with shoots after 8 weeks | Proportion (%) of explants with roots after 8 weeks |
|---|---|---|---|---|
| 0 | 99.1 | 0.6 | 13.5 | 5.4 |
| 0.032 | 100 | 0 | 72.9 | 7 |
| 0.25 | 100 | 12.5 | 40 | 10 |
| 2 | 100 | 24 | 76.9 | 46.3 |
| 15 | 0 | 0 | 0 | 0 |

<Example 2> Regeneration of Tomato

1. Preparation of Explant (1) Tomato seeds (available from Asia Seed Co., Ltd.) from which the seed coat was removed were treated in 70% ethanol for 1 minute, washed with distilled water, treated with 1% sodium hypochloride for 15 minutes, and washed with distilled water to prepare sterilized seeds.

(2) The sterilized tomato seeds were sown into a germination medium adjusted to pH 5.6 and incubated for 9 days in a growth chamber under conditions of a temperature of 25° C., a humidity of 50%, and a photoperiodic cycle of 16-hours light treatment and 8-hours dark treatment. The germination medium was prepared by mixing 4405.18 mg of MS salt (manufactured by Duchefa), 30 g of sucrose (manufactured by Duchefa), 500 mg of MES (manufactured by Duchefa), and 8 g of phyto agar (manufactured by Duchefa), per 1 L of distilled water.

(3) Cotyledons obtained through the incubation were cut into pieces having a size of 0.5 cm² to prepare explants.

2. Regeneration of Explant (Shoot Induction and Root Induction)

(1) For shoot induction, the explants were transferred to the shoot induction medium and then cultured for 4 weeks in a growth chamber under conditions of a temperature of 25° C., a humidity of 50%, and a photoperiodic cycle of 16-hours light treatment and 8-hours dark treatment. The shoot induction medium (pH 5.7) was prepared by mixing 4405.18 mg of MS salt (manufactured by Duchefa), 30 g of sucrose (manufactured by Duchefa), 1 mg of BAP (manufactured by Sigma), 0.5 mg of IAA (manufactured by Sigma), 500 mg of MES (manufactured by Duchefa), 8 g of phyto agar (manufactured by Duchefa), and Shungite, per 1 L of distilled water. The Shungite was produced near Lake Onega and purchased from the Karelian Shungite Factory in Russia. The Shungite was pulverized and screened through a screen with a mesh size of 1 to 3 mm to obtain a Shungite powder. The Shungite powder added to each medium composition was varied. The amounts of 0 g, 0.032 g, 0.25 g, 2 g, and 15 g of the Shungite powder were added to the respective medium compositions, per 1 L of distilled water.

(2) For root induction, the explants were transferred to the root induction medium from the shoot induction medium and then cultured for 4 weeks in a growth chamber under conditions of a temperature of 25° C., a humidity of 50%, and a photoperiodic cycle of 16-hours light treatment and 8-hours dark treatment. The root induction medium (pH 5.7) was prepared by mixing 4405.18 mg of MS salt (manufactured by Duchefa), 30 g of sucrose (manufactured by Duchefa), 500 mg of MES (manufactured by Duchefa), 8 g of phyto agar (manufactured by Duchefa), and Shungite, per 1

L of distilled water. The Shungite was produced near Lake Onega and purchased from the Karelian Shungite Factory in Russia. The Shungite was pulverized and screened through a screen with a mesh size of 1 to 3 mm to obtain a Shungite powder. The Shungite powder added to each medium composition was varied. The amounts of 0 g, 0.032 g, 0.25 g, 2 g, and 15 g of the Shungite powder were added to the respective medium compositions, per 1 L of distilled water. In each of the shoot induction medium and the root induction medium, the same amount of Shungite was used. For example, when 0.032 g/L of Shungite was used for the shoot induction medium, 0.032 g/L of Shungite was also used for the root induction medium.

3. Evaluation of Tomato Regeneration Efficiency (1) After the shoot induction from the explants (4 weeks after the beginning of explant regeneration), the number of explants with callus and the number of explants with shoots were counted. In addition, after the root induction from the explants (8 weeks after from the beginning of explant regeneration), the number of explants with shoots and the number of explants with roots were counted. The counted numbers were compared with the number of explants used for plant regeneration and are shown in Table 2.

(2) Referring to Table 2, when 0.032 to 2 g/L of Shungite is additionally included in the shoot induction medium and the root induction medium used in the process of regeneration of tomato explants, the shoot formation rate and the root formation rate were remarkably increased within an earlier period (i.e., 8 weeks) which is shorter than a typical tomato regeneration period (i.e., 14 to 16 weeks).

TABLE 2

| Shungite (g/L) | Proportion (%) of explants with callus after 4 weeks | Proportion (%) of explants with shoots after 4 weeks | Proportion (%) of explants with shoots after 8 weeks | Proportion (%) of explants with roots after 8 weeks |
|---|---|---|---|---|
| 0 | 96 | 0 | 12.2 | 8 |
| 0.032 | 100 | 24 | 76.5 | 35.3 |
| 0.25 | 100 | 14 | 74.3 | 14.3 |
| 2 | 100 | 40 | 77.1 | 37.1 |
| 15 | 0 | 0 | 0 | 0 |

<Example 3> Regeneration of Chrysanthemum

1. Preparation of Explant (1) Leaves of chrysanthemum-yellow plants (available from Cosmos Flower Garden, Korea) were treated in 70% ethanol for 1 minute, washed with distilled water, treated with 1% sodium hypo chloride for 15 minutes, and washed with distilled water to prepare sterilized leaves.

(2) The sterilized leaves thus obtained were cut into pieces having a size of 0.5 cm$^2$ to prepare explants.

2. Regeneration of Explant (Shoot Induction and Root Induction)

(1) For shoot induction, the explants were transferred to the shoot induction medium and then cultured for 4 weeks in a growth chamber under conditions of a temperature of 25° C., a humidity of 50%, and a photoperiodic cycle of 16-hours light treatment and 8-hours dark treatment. The shoot induction medium (pH 5.7) was prepared by mixing 4405.18 mg of MS salt (manufactured by Duchefa), 30 g of sucrose (manufactured by Duchefa), 1 mg of BAP (manufactured by Sigma), 0.5 mg of IAA (manufactured by Sigma), 500 mg of MES (manufactured by Duchefa), 8 g of phyto agar (manufactured by Duchefa), and Shungite, per 1 L of distilled water. The Shungite was produced near Lake Onega and purchased from the Karelian Shungite Factory in Russia. The Shungite was pulverized and screened through a screen with a mesh size of 1 to 3 mm to obtain a Shungite powder. The Shungite powder added to each medium composition was varied. The amounts of 0 g, 0.032 g, 0.25 g, and 2 g of the Shungite powder were added to the respective medium compositions, per 1 L of distilled water.

(2) For root induction, the explants were transferred to the root induction medium from the shoot induction medium and then cultured for 4 weeks in a growth chamber under conditions of a temperature of 25° C., a humidity of 50%, and a photoperiodic cycle of 16-hours light treatment and 8-hours dark treatment. The root induction medium (pH 5.7) was prepared by mixing 4405.18 mg of MS salt (manufactured by Duchefa), 30 g of sucrose (manufactured by Duchefa), 500 mg of MES (manufactured by Duchefa), 8 g of phyto agar (manufactured by Duchefa), and Shungite, per 1 L of distilled water. The Shungite was produced near Lake Onega and purchased from the Karelian Shungite Factory in Russia. The Shungite was pulverized and screened through a screen with a mesh size of 1 to 3 mm to obtain a Shungite powder. The Shungite powder added to each medium composition was varied. The amounts of 0 g, 0.032 g, 0.25 g, and 2 g of the Shungite powder were added to the respective medium compositions, per 1 L of distilled water. In each of the shoot induction medium and the root induction medium, the same amount of Shungite was used. For example, when 0.032 g/L of Shungite was used for the shoot induction medium, 0.032 g/L of Shungite was also used for the root induction medium.

3. Evaluation of Chrysanthemum Regeneration Efficiency (1) After the shoot induction from the explants (4 weeks after the beginning of explant regeneration), the number of explants with callus and the number of explants with shoots were counted. In addition, after the root induction from the explants (8 weeks after from the beginning of explant regeneration), the number of explants with shoots and the number of explants with roots were counted. The counted numbers were compared with the number of explants used for plant regeneration and are shown in Table 3. However, in Table 3, the number of explants for each medium represents the average number of explants for the cases where the amount of the Shungite was 0.032 g/L, 0.25 g/L, and 2 g/L, respectively.

(2) Referring to Table 3, when 0.032 to 2 g/L of Shungite is additionally included in the shoot induction medium and the root induction medium used in the process of regeneration of chrysanthemum explants, the shoot formation rate and the root formation rate were remarkably increased within an earlier period (i.e., 8 weeks) which is shorter than a typical chrysanthemum regeneration period (i.e., 16 to 18 weeks).

TABLE 3

| Shungite (g/L) | Proportion (%) of explants with callus after 4 weeks | Proportion (%) of explants with shoots after 4 weeks | Proportion (%) of explants with shoots after 8 weeks | Proportion (%) of explants with roots after 8 weeks |
|---|---|---|---|---|
| 0 | 100 | 0 | 2 | 0 |
| 0.032-2 | 100 | 15.3 | 19.8 | 9.9 |

Hereinabove, the applicant has described the preferred embodiments of the present invention, but these embodiments are presented only for illustrative purposes to help implementation of the technical idea of the present invention. Thus, any other changes and modifications should be interpreted as falling within the scope of the present invention as long as the technical idea of the present invention is implemented.

The invention claimed is:

1. A plant regeneration method comprising: obtaining an explant from a plant; and culturing the explant in a medium for organogenesis of the plant, wherein the medium comprises Shungite equal to or smaller than 3 mm and in a range of 0.032 to 5 g/L.

2. The method of claim 1, wherein the medium comprises MS salt,
   a carbon source, a cytokinin-based hormone, an auxin-based hormone, and distilled water.

* * * * *